US008574916B2

(12) United States Patent
Natan et al.

(10) Patent No.: US 8,574,916 B2
(45) Date of Patent: Nov. 5, 2013

(54) MELAMINE ASSAY METHODS AND SYSTEMS

(75) Inventors: Michael J. Natan, Los Altos, CA (US); Richard Griffith Freeman, Mountain View, CA (US); William E. Doering, Mountain View, CA (US); Rebecca Stoermer Golightly, Belmont, CA (US)

(73) Assignee: Cabot Security Materials Inc., Boston, MA (US)

( * ) Notice: Subject to any disclaimer, the term of this patent is extended or adjusted under 35 U.S.C. 154(b) by 202 days.

(21) Appl. No.: 13/124,808

(22) PCT Filed: Nov. 17, 2009

(86) PCT No.: PCT/US2009/064852

§ 371 (c)(1), (2), (4) Date: Apr. 18, 2011

(87) PCT Pub. No.: WO2010/057212

PCT Pub. Date: May 20, 2010

(65) Prior Publication Data

US 2011/0207231 A1 Aug. 25, 2011

Related U.S. Application Data

(60) Provisional application No. 61/115,360, filed on Nov. 17, 2008.

(51) Int. Cl.
*G01N 33/00* (2006.01)
*G01J 3/44* (2006.01)

(52) U.S. Cl.
USPC ................. 436/98; 436/96; 436/91; 356/301; 356/300

(58) Field of Classification Search
USPC ......................... 436/98, 96, 91; 356/301, 300
See application file for complete search history.

(56) References Cited

U.S. PATENT DOCUMENTS 5,693,152 A 12/1997 Carron
6,514,767 B1 2/2003 Natan
6,861,263 B2 3/2005 Natan
7,192,778 B2 3/2007 Natan
7,443,489 B2 10/2008 Natan
2005/0250159 A1 11/2005 Su et al.
2006/0147941 A1 7/2006 Su

FOREIGN PATENT DOCUMENTS

WO WO 2007/059514 5/2007

OTHER PUBLICATIONS

Liu, Yongliang et al. "Potential of Raman Spectroscopy and Imaging Methods for Rapid and Routine Screening of the Presence of Melamine in Animal Feed and Foods", Jan. 2, 2009, Applied Spectroscopy, vol. 63, No. 4, pp. 447-480.
Yang, Shuiping et al., "Detection of Melamine in Milk Products by Surface Desorption Atmospheric Pressure Chemical Ionization Mass Spectrometry" , 2009, Analytical Chemistry, 81 (7) 2426-2436.
Ai, Kelong et al., "Hydrogen-Bonding Recognition-Induced Color Change of Gold Nanoparticles for Visual Detection of Melamine in Raw Milk and Infant Formula" 2009, JACS Communications.
Lin, M. et al., "Detection of Melamine in Gluten, Chicken Feed, and Processed Foods Using Surface Enhanced Raman Spectroscopy and HPLC", 2008, Journal of Food Science, vol. 73, Nr. 8, pp. 129-134.
He, Lili et al., "A new approach to measure melamine, cyanuric acid, and melamine cyanurate using surface enhanced Raman spectroscopy coupled with gold nanosubstrates", 2008, Sens & Instrumen. Food Qual. 2:66-71.
International Search Report and Written Opinion mailed Feb. 4, 2010 for PCT/US2009/064852.
Koglin, "Adsorption and Displacement of Melamine at the Ag/Electrolyte Interface Probed by Surface-Enhanced Raman Microprobe Spectroscopy", 1996, Journal of Physical Chem., vol. 100, p. 5078.
Ju et al., "The Fragmentation of Melamine: A study via Electron-Impact Ionization, Laser-Desorption Ionization, Collision-Induced Dissociation, and Density functional Calculations of Potential Energy Surface", 1999, Journal of Physical Chem., vol. 103, pp. 582-596.
Weibenbacher et al., "Surface enhanced Raman spectroscopy as a molecular specific detection system in aqueous flow-through systems", May 1998, Analyst, vol. 123, pp. 1057-1060.

*Primary Examiner* — Christine T Mui
(74) *Attorney, Agent, or Firm* — Swanson & Bratschun, LLC

(57) ABSTRACT

A method of detecting melamine which includes providing a quantity of SERS-active particles and mixing the SERS-active particles with a solution containing melamine. The method further includes detecting a surface enhanced Raman spectrum of the melamine. The foregoing method may optionally include aggregating the SERS-active particles. Aggregation may occur before or after the SERS-active particles are mixed with a solution containing melamine. The method of detecting melamine may optionally include concentration of the SERS-active particles. The method may further include mixing a chaotropic agent having a higher affinity for a selected binding site than melamine into the solution containing melamine. The method may further include mixing a quantity of a SERS-active standard having a known SERS spectrum with the solution containing melamine and SERS-active particles. Assay apparatus and systems are also disclosed.

22 Claims, 11 Drawing Sheets

MELAMINE ASSAY METHODS AND SYSTEMS

RELATED APPLICATIONS

This application is a 35 U.S.C. §371 national phase application of PCT/US2009/064852 (WO 2010/057212), filed on Nov. 17, 2009, entitled "Melamine Assay Methods and Systems", which application claims the benefit of U.S. Provisional Application Ser. No. 61/115,360, filed Nov. 17, 2008, which is incorporated herein by reference in its entirety.

TECHNICAL FIELD

The embodiments disclosed herein include methods and systems to carry out an assay or test or measurement for the identification or quantitation of for melamine (M), or for other molecules which are contaminants in food, pet food, drugs, cosmetics, or other materials. One embodiment is a method for identification and quantitation of melamine in dairy products, and more particularly in milk.

BACKGROUND

Melamine has occurred as a contaminant in food, pharmaceuticals and other consumer products. Known assays for the detection of melamine may be undesirable or ineffective for reasons including, but not limited to, cost, difficulty of use, inaccuracy, delay before achieving results, reliance upon sophisticated laboratory equipment or other assay problems and challenges. The present invention is directed toward overcoming one or more of the problems discussed above.

SUMMARY

Figure 1:
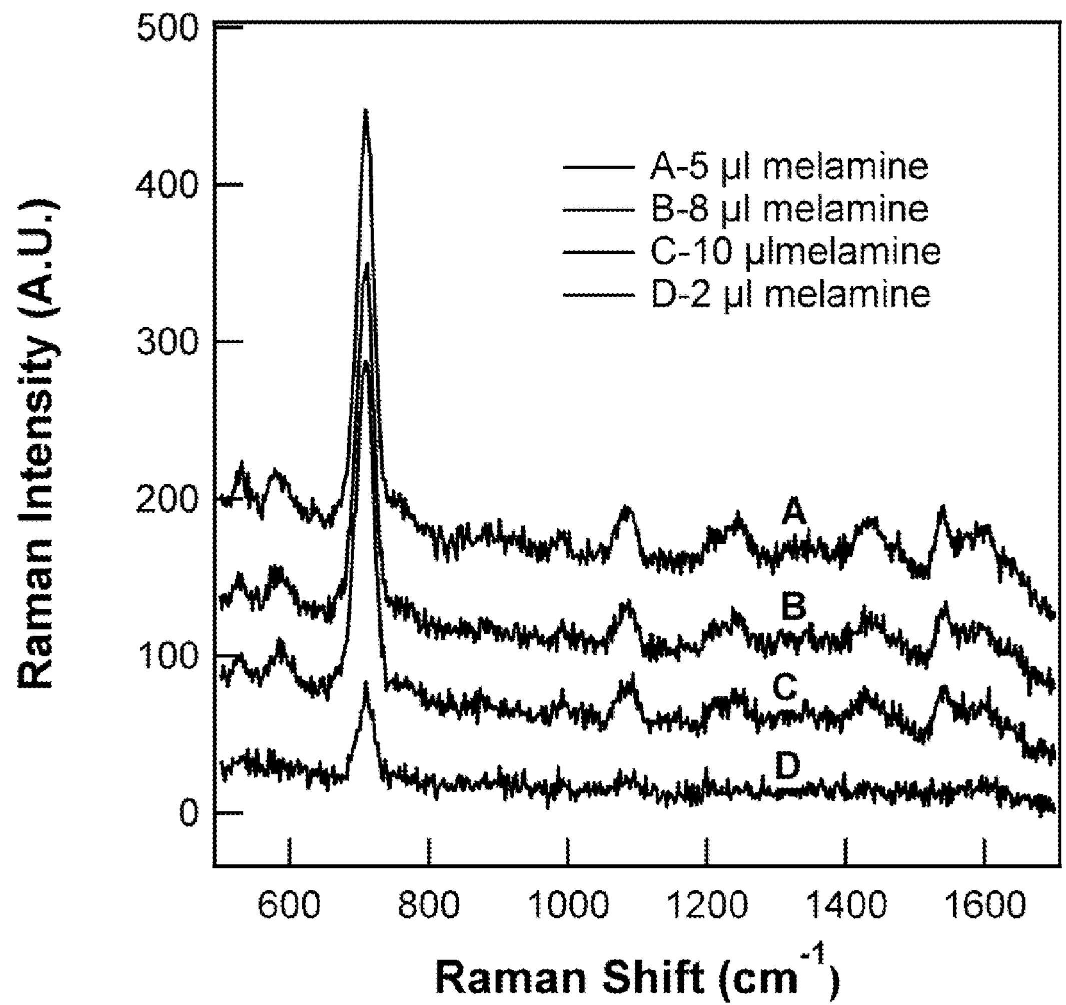
FIG. 1 is a graphic representation showing the detection of a SERS signal of melamine in water.

The disclosed embodiments use surface enhanced Raman spectroscopy (SERS) for detection. The embodiments use metal nanoparticles as the SERS-active surface. In some cases, the detection is direct, relying on the SERS spectrum of melamine or another substance for identification or quantitation. In other cases, detection is indirect, relying on the spectroscopic signature of another substance or molecule. Combinations of direct and indirect detection are also disclosed. In yet other cases, detection is based on a SERS signal from a label such as a SERS nanotag as described in U.S. Pat. Nos. 6,514,767, 7,192,778, and 7,443,489, each of which is incorporated fully herein for all teaching of the use of SERS nanotags as described herein.

In some cases, the SERS-active surface may be a single particle. In other cases, it may be an aggregate of particles. In yet other examples, it may be a mixture of single and aggregated particles. The SERS-active surface can also be a monolayer or multilayer of particles, a microscopic or macroscopic surface prepared by evaporation, electrochemical methods, electroless plating, various forms of lithography, microcontact printing, or any of the other known methods to make SERS-active materials, provided the resulting materials are dispersable. The dimensions of the dispersable SERS-active surface can be as small as 5 nm, and as large as 0.09 $cm^2$. The SERS-active surface can be excited in the ultraviolet (e.g. for Al), or the visible, or the near-IR, or the IR.

Various methods of detecting a molecule or substance of interest are disclosed. In addition, assay apparatus and systems are disclosed. One embodiment is a method of detecting melamine which includes providing a quantity of SERS-active particles and mixing the SERS-active particles with a solution containing melamine. The method further includes detecting a surface enhanced Raman spectrum of the melamine. The foregoing method may optionally include aggregating the SERS-active particles. Aggregation may occur before or after the SERS-active particles are mixed with a solution containing melamine.

The method of detecting melamine may optionally include concentration of the SERS-active particles. Concentration may be advanced by using an aggregating agent and mechanically concentrating the mixture, using magnetic concentration techniques or through other known concentration steps.

The method may further include mixing a chaotropic agent having a higher affinity for a selected binding site than melamine into the solution containing melamine. Optionally, the chaotropic agent will exhibit a minimal SERS spectrum.

The method may further include mixing a quantity of a SERS-active standard having a known SERS spectrum with the solution containing melamine and SERS-active particles. In this alternative embodiment a surface enhanced Raman spectrum of the SERS-active standard may be detected along with the spectrum of the melamine. The SERS-active standard may be a SERS nanotag, a SERS-active substance or another material. In certain embodiments it may be desirable to implement the SERS-active standard with a chemical analog for the material being detected. For example, the SERS-active standard may be deuterated melamine in an assay for melamine detection.

An alternative embodiment is a method of detecting melamine as described above where the SERS-active particles are associated with a quantity of magnetic particles. In this embodiment the magnetic particles, SERS-active particles and melamine or other analyte may be concentrated with a magnetic particle concentrator. The SERS-active particles may be associated in solution with the magnetic particles through electrostatic attraction between the particles or by other means. Alternatively, the SERS-active particles may be associated with the magnetic particles prior to mixture with the melamine containing solution. Chaotropic agents or SERS-active standards may be used with this embodiment as well, as described above.

An alternative embodiment is a method of detecting a molecule of interest. This method includes mixing a quantity of SERS-active particles, a quantity of a SERS-active standard, and a solution containing the molecule of interest. The resulting mixture may optionally be concentrated, for example, with a magnetic particle concentrator. The method may further include detecting the surface enhanced Raman spectrum of the molecule of interest and the surface enhanced Raman spectrum of the standard. The SERS-active standard may be an analog of the molecule of interest. For example, if the molecule of interest is melamine the SERS-active standard may be deuterated melamine.

Alternative embodiments include apparatus, assays, systems and kits having compounds and components required to implement the methods described above.

DETAILED DESCRIPTION

Several different assay formats are described herein, each of which can be used for detection and/or quantitation of melamine or similar substances of interest. The assay formats generally include colloid-based assays (see methods A1 and A2 below); colloid-based assays involving magnetic concentration (methods B1, B2, and B3), and SERS nanotag assays (method C). As described below, each of these basic assay formats have a number of variations.

Method A1

In Method A1 a solution containing melamine is added to a solution of SERS-active particles, or applied to some other dispersable SERS-active substrate. The solution containing melamine might represent an extract, or might otherwise have a higher purity than the original melamine-containing sample. In other cases, the solution might contain a higher concentration of free (unbound or uncomplexed) melamine. In yet other cases, the original melamine-containing sample, such as milk, might be added directly or after dilution.

The particles to which the melamine-containing solution is added could be of a single type, or could be a mixture of different types of particles. The composition of the particles could be a single material such as Au, Ag, Cu, Al, or some other SERS-active metal, or it could be an alloy of two or more SERS-active materials. The particle could be of core-shell geometry, with a core comprising one material, and a shell comprising another. For example, the core might be a 20-nm diameter Ag particle, with the shell a 0.5 nm-thick coating of $Al_2O_3$. Alternatively, the core might be a 50-nm thick $SiO_2$ particle, with a 3-nm thick Au shell. Likewise, the particle could be of the core-inner shell-outer shell variety, an example being a 50-nm diameter Au core, a 2-nm thick $SiO_2$ inner shell, and 5-nm thick Au outer shell. The particle could be of roughly spherical symmetry, or it could be highly anisotropic, examples of anisotropic shapes include but are not limited to rods, plates, prisms, cylinders, stars, and tetrahedral. The particle could be solid, or could be porous, such as the material resulting when the Ag is dissolved from an Au/Ag alloy. A mixture of particle types can also be used, such as 12-nm Au spheres and 90-nm Au spheres, or 5-nm diameter Ag prisms and Au hollow cubes with 50-nm edge lengths.

When a solution containing melamine is added to the particles, some aggregation of the SERS-active particles occurs. As used herein, an aggregate is defined as 2 or more but less than 10,000 particles in very close proximity. For example, if there were 100 isolated particles in solution, and by one means or another, as described more fully below, the solution were to comprise 98 isolated particles and two particles in very close proximity, close proximity being defined as joined, touching, or permanently less than ½ the particle diameter away from one another, the solution would be said to be aggregated.

Such aggregation might be instantaneous, or might require time to occur. Some of the particles or all of the particles may be involved. Alternatively, some aggregation might be induced by external means, either physical or chemical. For example, the aggregation might be brought about by sample heating, cooling, sonication, stirring, or mixing. Alternatively, aggregation may be initiated by addition of an aggregating agent such as a solution of NaCl. This aggregating agent (either in solution or as a solid) might be added prior to the melamine-containing solution, or after the melamine-containing solution. In another approach, a solution of aggregating agent or a solid aggregating agent is mixed with the melamine-containing sample, and then mixed with the SERS-active particles.

The SERS-active particle solution might be added to the melamine-containing solution, or vice versa, or alternatively the two solutions could be introduced simultaneously into a common area or volume.

In any of the above scenarios, melamine becomes adsorbed to the SERS-active particles, either to individual particles or aggregates or both, and is detected by detecting the surface enhanced Raman spectrum of the melamine. The detection of melamine might involve just aggregated particles, or it could involve both aggregated and isolated particles, or it could involve just isolated particles.

Method A2

This approach is identical to the above except that no aggregation occurs. There are several routes by which aggregation could be avoided. In one approach, the solution from which the detection takes place may contain only isolated SERS-active particles because the isolated SERS-active particles that were mixed with the melamine-containing solution at all times remain isolated. Alternatively, the solution containing the SERS-active particles may already contain aggregates, or a mixture of isolated particles and aggregates, and no further aggregation occurs. For example, if the solution initially contains 98 isolated SERS-active particles and one aggregate containing 2 SERS-active particles, and after addition of the melamine-containing solution finally contains 98 isolated SERS-active particles and one aggregate containing 2 SERS-active particles, no further aggregation has occurred. The detection of melamine may occur by obtaining the surface enhanced Raman spectrum of melamine. Detection might involve just aggregated particles, or it could involve both aggregated and isolated particles, or it could involve just isolated particles.

Method B1

An alternative embodiment is to use magnetic particles to concentrate the SERS signal from melamine. In one approach, the difference in charge between aggregated or individual SERS-active nanoparticles and magnetic particles is exploited. The magnetic particle is typically of the core-shell variety that is widely used in biological assays, with a magnetic core and non-magnetic shell. Alternative magnetic particle configurations may be used as well. The overall particle dimensions could be as small as 5 nm or as large as 10 microns, with the magnetic core being of dimensions between 3 nm and 9 microns. The core could comprise a single magnetic particle, or could consist of multiple particles. The shell could be a polymer, an oxide, or some other material. The magnetic particle could be SERS-active, comprising a magnetic core, a polymeric or glass first shell, and SERS-active second shell.

In this type of embodiment, the assay begins as in Method A1 or A2 above, but the resulting solution, possibly containing melamine and adsorbed or otherwise bound to a SERS-active surface, is mixed with a solution containing magnetic particles. This mixture can result from addition of SERS-active particles to magnetic particles, from addition of magnetic particles to the SERS particle solution, or by simultaneous addition of solutions of both particle types in separate vessels to a third vessel. In each case, the magnetic particles and SERS-active particles may be oppositely charged and bind to one another through electrostatic forces. After a certain period of time, anywhere between 1-10,000 seconds, a magnetic field may be applied to the particle mixture, and the magnetic particles are concentrated at a particular location defined by the magnetic field. The pellet of concentrated particles may then be optically interrogated, and a SERS signal corresponding to melamine may be acquired from the electrostatically bound SERS-active particles. It is not necessary that all of the SERS-active particles be bound electrostatically to the magnetic particles. Likewise, it is not necessary for all the magnetic particles to be concentrated in the pellet.

There are many methods other than simple electrostatic binding to bring a sufficient quantity of the SERS-active particles and magnetic particles together. For example, an electrostatic interaction could be triggered by a separate reaction, for example by a photochemical reaction that generates a charge on one or another particle. Alternatively, dative bonds or metal-ligand bonds could be used. For example, the presence of thiol (RSH) groups on the surface of the magnetic particles will cause the binding of Au nanoparticles via formation of RS—Au bonding interactions. Alternatively, the particles may be prepared or selected to covalently bind, for example, each particle type may have a different, stable surface-bound functional group that is reactive toward the functional group of the corresponding particle. Recently, such types of functional groups reactions have been developed for organic molecules (e.g. click chemistry) and for biomolecules inside cells.

Prior to concentration, the magnetic particles may be isolated from one another, or the magnetic particles may consist entirely of aggregates, or the magnetic particles could be a mixture of isolated particles or aggregates. Alternatively, the particles might be isolated prior to concentration and become partly or entirely aggregated during concentration.

Method B2

In this alternative approach, SERS-active particles are bound to the magnetic particles prior to introduction of the melamine-containing sample, so that there are no or very few free SERS-active particles at the time the melamine-containing sample is introduced. Such magnetic particle-SERS particle assemblies might be made in advance and comprise a single reagent, or such assemblies might be made in situ. The SERS-active particles might be bound by electrostatic forces, or by the covalent binding methods described above. There may alternatively be a coating or gel on the magnetic particles, with the SERS-active particles incorporated into the coating or gel. The SERS-active particles might be isolated from one another, or they could be aggregates, or they could be a mixture of isolated particles or aggregates. Alternatively, the SERS-active could initially be bound isolated particles that become a bound aggregate by addition of the melamine-containing solution or by an aggregating agent. For example, in a solution initially containing 100 magnetic particles, each of which contains 50 bound isolated particles, the addition of the melamine-containing solution or an aggregating agent might cause aggregation on one of the magnetic particles, leading to 99 magnetic particles that harbor 50 isolated SERS-active particles, and 1 magnetic particle that contains 48 isolated-SERS-active particles and one dimer of SERS-active particles.

Prior to concentration, the magnetic particle-SERS particle assemblies may be isolated from one another, or the magnetic particles may consist entirely of aggregates, or the magnetic particles could be a mixture of isolated particles or aggregates. Alternatively, the particles might be isolated prior to concentration and become partly or entirely aggregated during concentration.

The melamine-containing sample might be added to a solution of magnetic particle-SERS particle assemblies, or vice versa, or both might be introduced simultaneously into a common area or volume. In this method, the concentration of magnetic particles and subsequent detection would then follow as described above.

Method B3

This method combines aspects of Method B1 and Method B2. In this embodiment, there are SERS-active particles bound to the magnetic particles prior to introduction of the melamine-containing sample and also SERS-active particles in solution that become bound after introduction of the melamine-containing sample. As above, the SERS-active particles in solution and those on the magnetic surface might be isolated particles, aggregates, or a combination of isolated and aggregated particles. The binding of the SERS-active particles to the magnetic particles in solution might occur to the magnetic particle itself, and not involve the already-bound SERS-active particles, or alternatively the SERS-active particles in solution might bind to an already-bound SERS-active particle. If such surface-bound SERS-active particles were isolated particles, binding of the SERS-active particles from solution would generate surface-bound aggregates. Alternatively, if the surface bound particles comprised as least one aggregate, binding of the SERS-active particle from solution would increase either the number of size of surface-bound aggregates, or both. In another implementation, the SERS-active particles in solution might bind to both the surface-bound SERS-active particles and to the magnetic particle itself.

There are numerous methods of mixing the magnetic particles harboring surface-bound SERS-active particles (X), the SERS-active particles in solution (Y), and the melamine-containing sample (Z). For example, Y could be added to Z, (Y+Z), or Z could be added to Y (Z+Y), and either could be added to X (Y+Z+X or Z+Y+X, respectively). Alternatively, X could be added to the resulting mixtures (X+Y+Z or X+Z+Y). The disclosed methods incorporate all possible mixing combinations, including simultaneous introduction of all three materials into a common area or volume.

Method C

Another method involves indirect direction, using a SERS-active label, for example a SERS nanotags. Such a label comprises a SERS-active core metal particle, an adsorbed reporter molecule, and an encapsulant, as described in U.S. Pat. Nos. 6,514,767, 7,192,778 7,443,489, 6,514,767; and 6,861,263 each of which is incorporated fully herein by reference for all matters disclosed therein. In one indirect detection approach, a first capture reagent is bound to a magnetic particle, and a second capture reagent is bound to a SERS nanotag. If melamine binds to both capture agents at once, the SERS nanotag becomes immobilized on the surface of the magnetic particle, and can be concentrated as described above. In this case, the detection is of the SERS nanotag, and the signal intensity is proportional to amount of melamine in the sample.

This approach is analogous to sandwich-based approaches for detection of proteins. For protein detection, the capture reagents are typically antibodies, and the assay format is typically referred to as a sandwich immunoassay. Likewise, similar schemes utilize for oligonucleotides, with the capture reagents typically comprising a pair of DNA sequences, each of which having base-pairing complementarity to one end of the oligonucleotide being detected.

There are a number of variations of the protein and oligonucleotide assays described above. For example, in a competitive immunoassay, introduction of an analyte to be detected causes disruption of a pre-formed complex. This embodiments disclosed herein specifically include all such assay variations. In one non-limiting example, a melamine analog could be bound covalently to a magnetic particle and to a capture agent on one or more SERS nanotags. Introduction of melamine could lead to disruption of the capture agent-melamine analog-capture agent sandwich, leading to a decrease in the number of SERS nanotags bound to magnetic particles, generating a corresponding decrease in SERS intensity. In such an assay format, the signal intensity is inversely proportional to the amount of melamine in the sample. The methods of this disclosure include all assay format variations previously described in the literature for detection of proteins, DNA, cells, or low-molecular weight species.

Sample Pre-Treatment/Sample Preparation

In some cases, it may be necessary to carry out sample pre-treatment to make melamine more available for analysis. For example, in some cases melamine may be tightly bound to a protein present in milk, a drug, a consumer product or another substance, so that the free concentration measured would be less than the actual concentration. In measurements involving extensive sample preparation and long analysis times, e.g. High-performance liquid chromatography, HPLC, the addition of a sample preparation step to dislodge bound melamine does not add significantly to the already-long analysis time. However, for point-of-use, in-the-field, and/or rapid analysis, a separate sample pre-treatment step is not desirable.

Thus, methods are disclosed whereby any sample preparation is carried out rapidly and in the same container as other assay steps. One approach is to disrupt the binding between melamine and its binding site. This can be done by introduction of a "disruptor", a species that binds to the melamine binding site and thereby making freed melamine more available for analysis. The disruptor could work by having a higher affinity for the site than melamine. Alternatively, it could have a lower affinity, but be present at much higher concentrations. The concept of disruptors is known, and is often referred to as chaotropic agents. A novel embodiment disclosed herein is the use of non-SERS-active disruptors. A non-SERS-active disruptor is a species that acts as disruptor but that does not adsorb strongly to SERS-active surfaces, or adsorbs but only weakly, or adsorbs but has a very weak SERS spectrum. Thus, in the assay formats described above that rely on direct detection of melamine by SERS, it is important that the disruptor not exhibit a strong SERS spectrum, and ideally not even bind to the surface of SERS-active particles. Such disruptors could be introduced to samples containing melamine prior to mixing with SERS-active particles, or afterwards, or simultaneously. Note also that disruptors can be used in the indirect assay formats based on detection with SERS nanotags, though in that instance, binding of disruptor to the SERS-active surface is not an issue as the latter is typically protected by an encapsulant.

Other methods can be used to eliminate binding of melamine to a matrix component. For example, heat can be used. The heat can be delivered globally, i.e. microwave irradiation, or it can be delivered locally, for example by plasmon absorption-induced heating of metal nanoparticles.

Aggregating Agents

A variety of substances including but not limited to aqueous NaCl can be used to aggregate particles. In particular, NaBr, NaI or other sodium salts can be used. Likewise, KCl, LiCl, other chloride salts can be used. In other instances, salts that contain neither sodium nor chloride (e.g. KBr) can be used. In yet other examples, divalent cations (e.g. $Ca^{2+}$ or $Mg^{2+}$) can be used or divalent anions (e.g. sulfide). Trivalent cations e.g. $Ce^{3+}$ can also be used to promote aggregation.

In some cases, the aggregating agent does not have to be ionic. For example, certain organic solvents will aggregate aqueous solutions of metal nanoparticles. Likewise, the aggregating agent need not be chemical in nature. For example, under certain conditions, heat, cold, or light can induce particle aggregation.

Capture Agent/Recognition Motifs

Any number of capture agent and recognition motifs could be used for detection of melamine (M) using any of the above assay formats.

One approach exploits cyanuric acid (CA), which complexes strongly to melamine using multiple hydrogen bonding interactions that are very similar to those used in DNA base pairing. For example, one could introduce an alkyl group into cyanuric acid, and put a functional group on the end of the alkyl chain to enable it to be tethered to a magnetic particle surface. A magnetic particle so functionalized could be added to a sample containing melamine, generating a surface-bound CA-M complex that could then be detected by SERS through a variety of mechanisms described above.

Given that CA and M are known to form infinite networks of CA-M-CA-M-CA-M- etc., one could also surface confine CA as described above to both magnetic particles and SERS nanotags, and carry out an indirect assay based on formation of magnetic particle-CA/M/CA-SERS nanotag sandwiches. Alternatively, the SERS nanotag could be replaced by CA bound to a SERS-active particle, enabling several of the direct detection formats described above. For example, an —OH group of CA can be replaced by an —SH group, generating a species that will both bind to a SERS-active particle and form strong complexes with M.

Complexes of CA-M can also serve as the entity captured or recognized. Thus, one could generate pairs of antibodies that are selective for the CA-M complex. Likewise, by analogy to triplex formation of oligonucleotides, a species T could be added to form triplexes of the form T-CA-M, or CA-M-T, or M-T-CA, Such capture and recognition motifs are not confined to cyanuric acid. There are any number of organic molecules that will form complexes with melamine. Moreover, it is not necessary to use the same motifs on both magnetic and SERS-generating particles: each can have a different capture or recognition agent.

In fact, it is not even necessary to have two such reagents, as there are a number of assay formats that depend only on one such species. For example, an aptamer could be generated that binds tightly to melamine, and also binds the melamine to the surface of a SERS-active particle. One could then directly detect binding of melamine by SERS using any of the formats described above.

If the capture agent or agents have a measurable SERS spectrum, it can be subtracted out of the spectrum generated in the presence of melamine. Alternatively, one embodiment includes the development of capture agents that are both selective for melamine and have weak or no (measurable) SERS spectrum.

A variety of other classes of capture reagents are known, and can applied to detection of melamine. For example, melamine can bind in the cavity of certain cyclodextrins, and cyclodextrins can be modified so they will bind covalently to magnetic particles or via thiolate groups to SERS-active surfaces. Cryptands and cryptates are other examples of molecular entities that could recognize melamine. Likewise, supramolecular assemblies that could bind to melamine may be exploited as capture agents.

Capture and recognition motifs do not have to have to be molecular in nature, polymers and similar substances could also be used as capture agents. For example, a polymer comprising an alkyl backbone and CA pendant groups will bind strongly to melamine. Alternatively, one can use molecularly-imprinted polymers (MIPs) directed toward melamine to extract and bind it from samples. Alternatively, a polymer might simply exclude certain species as opposed to specifically binding melamine. For example, a thin coating of polydimethylsiloxane (PDMS) improves the performance of SERS-active substrates in real-world aqueous biologically-related samples by preventing adsorption of anions (e.g. chloride, phosphate) that are present at high concentrations (e.g. mM) and bind strongly to metal surfaces. In another embodiment, the polymer need not bind at all to melamine, but rather be permselective. Here, melamine would diffuse through the polymer and reach SERS-active particle surface, but other, potentially interfering species, would not be able to diffuse through, blocked either by considerations of size, shape, charge, polarity, chemical functionality, or by a variety of these factors.

SERS Particle Motifs

Selected embodiments disclosed herein feature the use of a SERS-active particle-based assay for melamine. The particle based assays are functionally quite distinct from known planar substrate assays that have been previously described for melamine and the vast majority of analytical applications proposed for SERS. On planar substrates, a drop of a solution, potentially containing the analyte in question, is applied to the surface. Often, and particularly in the case of the melamine assays described in the recent literature, immobilization and/or adsorption of the analyte is driven by solvent evaporation. Laser excitation to the same spot allows the analyst to pinpoint the analyte location, effectively reducing the effective area of the substrate where the analyte can be present. This is an inefficient use of substrate, in that spot sizes are typically on the order of 0.1 mm in diameter, while substrates are typically on the order of 1 cm2.

An additional problem with a planar substrate approach is that the analyte might actually crystallize rather than adsorb at the particle surface. In this case, one is actually measuring a Raman spectrum instead of, or in addition to, a SERS spectrum. In the recent melamine papers, this is likely the case, insofar as the enhancement factors reported are extremely low. A further difficulty with this approach is that the Raman spectrum of the dried and/or crystallized analyte will necessarily be different than the SERS spectrum, since it is known that adsorption at SERS-active metal surfaces causes noticeable changes in peak locations and relative intensities.

Yet another problem with this approach is the need to either wait for solvent evaporation to occur, or to drive solvent evaporation with heat, the latter requiring an extra piece of equipment.

Macroscopic planar or near-planar substrates can be used without solvent evaporation. For example, one can place a SERS-active substrate in a sample containing analyte. However, given the typical minimum size of substrate required to allow it to be handled, this requires a large volume of analyte-containing solution, e.g. 5 mls, and thus sets a threshold on the lowest number of analyte molecules that can be detected, since the vast majority of molecules in the solution are not being interrogated in the SERS experiment. Alternatively, one can place a volume of sample directly on a substrate. However, it is necessary to have some way to contain the applied sample and prevent the liquid from spreading. This requires either a special apparatus, or modification to a SERS substrate (a simple example being the gluing of an O-ring to the surface).

When solvent evaporation is not used, another shortcoming of macroscopic SERS-active surfaces is the varying proclivity of analytes for binding to the surface. In some cases, the equilibrium constant for adsorption is sufficiently low that analyte coverage at the SERS hot spots is low.

A final issue with macroscopic, planar SERS-active substrates is limited dynamic range. Once monolayer coverage has been reached, a plot of signal intensity versus solution concentration is no longer linear and in fact becomes asymptotic: increasing concentrations lead to no change in observed signal.

The particle-based assays and dispersed substrate-based assays described herein overcome all of the aforementioned limitations associated with macroscopic SERS-active substrates. First, no additional instrumentation or sample processing is required, since the analyte is directly mixed with a solution that contains SERS-active particles in suspension, either free or associated with a magnetic particle or some other dispersed stationary phase. Second, particle based assays can be carried out with arbitrarily small sample volumes, e.g. 0.1 to 10 microliters. An optional magnetic concentration step also allows the assay to be carried out in very large volumes, e.g. 1 liter. Moreover, there is no need to physically contain the analyte-bearing solution, as is required with planar substrates, since the analyte solution is naturally contained in the vessel bearing the SERS-active nanoparticles.

Other embodiments of the assay formats described above feature variations in the composition and geometry of the SERS-active particles used, and in particular the choice of metal and choice of particle size and shape. For example, particles may be selected that either individually, or as aggregates, will exhibit a significant enhancement factor for SERS. In addition, particles may be selected or fabricated to enhance the extent to which analytes of interest will adsorb. It has been shown that certain crystal planes of Au and Ag are, for certain adsorbates, especially favored or disfavored. Since the prevalence of selected planes depends on particle geometry, it follows that particle geometry will impact the extent of adsorption and thus the overall signal strength observed.

To the extent one is using typical SERS substrates comprising Ag or Au, which are excited with visible or near-IR wavelengths, melamine itself will not be subject to surface enhanced resonance Raman scattering (SERRS). Melamine does not exhibit any extinction in the visible region of the electromagnetic spectrum, because melamine is non-resonant. However, it is possible to make complexes between melamine (M) and other non-resonant species (B), e.g. M+B, or M+B+M, or B+M+B, or related complexes or assemblies, where the complex itself is resonant. Thus, prior to the introduction of melamine, there is no resonant SERS associated with B. Sample introduction generates a complex that is resonant, significantly increasing the measured SERS intensity through SERRS.

Porous SERS particles with exceptionally high surface areas can also be used in any of the assays described above. Such particles can be made in a variety of ways, for example by Ag dissolution in composite Au/Ag particles.

Ratiometric Methods and Internal Standards

The use of internal standards in the form of SERS nanotags, SERS-active substances or other non-SERS-active internal standards for melamine and other assays is disclosed herein. The benefit of a standard in a SERS measurement is that it allows a ratiometric measurement to be made, for example, a ratio of the analyte signal (in this case for melamine) to that of a standard signal, thereby significantly lowering the measurement error. Standards are typically described as being internal (incorporated into the assay materials) or external (added separately).

The benefit of using a SERS nanotag of other SERS-active substance as an internal standard is that it has a fixed SERS spectrum. Suitable SERS-active standards can be any chemical composition or material having a known SERS spectrum. For example, substances including but not limited to trans-1,2-bis(4-pyridyl)ethylene (BPE), pyridine, 2-mercaptopyridine, 4,4'-dipyridyl (DPY) Raman dyes and inorganic or organic SERS-active substances may be used to implement an internal standard. Deuterated melamine may be a particularly effective internal standard substance in a melamine assay since deuterated melamine and melamine are likely to have similar binding affinities. SERS nanotags have an additional advantage for standards because encapsulated nanotags are is exceptionally stable to environmental factors such as temperature and ionic strength, generates an intense signal that can be tuned across the entire Raman spectrum, and SERS nanotags have a surface functionality (e.g. —OH or —SH) that allows them to be attached to other particles or surfaces.

Thus, one can add a fixed amount of SERS nanotags or a SERS standard substance to a solution of SERS-active particles, and use the resulting mixture for the assays of Method A1 or A2. In both cases, the there will be one or more SERS spectral feature associated with melamine, and one or more associated with the standard. Depending upon the concentration ranges of interest for melamine, the amount of standard can be adjusted such that separate signal intensities are comparable. In addition, the standard can be chosen so that the bands used for comparison are spectrally near or spectrally far from those of melamine. The latter might allow the use of a low-cost filter set instead of a high-cost spectrometer in the detector.

Likewise, SERS nanotags or another suitable standard material can be attached to the surface of magnetic particles, providing a fixed signal in assays of the Method B1, B2, or B3. Even in method C, which already employs SERS nanotags, a different tag or standard substance can be used as an internal standard, again by attachment to the surface of the magnetic particle. Also, one can use two internal standards in the same measurement, one in solution and one bound the magnetic particle surface.

The use of SERS nanotags or a SERS-active standard, which possess a fixed, tunable, and strong Raman signal as an internal standard, also provides benefit in assays primarily employing non-particle based SERS surfaces. For example, in an assay featuring SERS “wells” the standard can be encased in a well. For planar substrates, the standard can be covalently attached as low-coverage submonolayers to the surface. Any SERS measurements with aggregated Au, Ag, Cu or other SERS-active metal nanoparticles in solution can benefit from the addition of stable SERS standards. Thus, an alternative embodiment is the use of SERS standards as universal ratiometric standards for all SERS measurements, for all analytes, in all geometries.

Multiplexed Detection

The methods described herein can also be used for detection and quantitation of multiple analytes simultaneously. Each analyte can be interrogated using different chemistries. For example, one type of particle, with a particular recognition chemistry and particle configuration and assay format (e.g. no-wash), might be used for a certain analyte like melamine, while different recognition chemistry might be used with similar particle configurations and assay formats for a different analyte, e.g. a pesticide. Note that the same type of particle and excitation wavelength might be used for each analyte; alternatively a different type of particle (e.g. Au vs. Ag) and different excitation wavelength might be employed. In both cases, however, different Raman features, or combinations of features, are used to quantify the analytes.

Spectroscopic Techniques

It should be recognized that several other close related surface-enhanced processes can be used for melamine detection, all of which can be implemented using the methods described herein. These alternative spectroscopic techniques include but are not limited to surface enhanced infrared absorption spectroscopy (SEIRA) and surface enhanced hyperRaman scattering (SEHRS). For example, in SEHRS, pulsed 1500-nm excitation can be used, with detection of Stokes-shifted Raman photons between 750 and 900 nm.

Sample/Matrix

Another beneficial attribute of the methods disclosed herein is enhanced flexibility in the selection of the analyte-containing matrix that be used. The development of a SERS-based assay using milk is itself a significant improvement over the prior art, as the methods disclosed herein eliminate the need for an extraction step. Moreover, the disclosed assays can work with over a wide range of matrices, for example any number of milk-based substances, including but not limited to whole milk, cream, skim milk, partly-skim milk (e.g. 1%, 2% fat), and half-and-half. In addition, reconstituted powdered milk can be analyzed, and even powdered milk itself (without reconstitution) can be the subject of analysis. Likewise, dairy substances related to milk can be used, such as yogurt, curds, whey, and cheese. In addition, infant formula, either in powdered or reconstituted state, can be analyzed. Other related farm products such as eggs (after cracking) could also be tested.

Analysis for melamine or related impurities may also be extended to any number of ancillary substances, e.g. the packaging used for milk or the related dairy products described above, including glass, plastic and paper, fixtures for opening/closing/re-opening containers, and even straws.

Reader

The methods described herein may be implemented with a portable and/or handheld reader for molecular identification and quantitation using SERS. A number of designs for portable Raman instrumentation have been described and are commercially available. Applications involving known readers have been focused either on acquisition of normal Raman spectra (which are then often compared to reference spectra in a stored library), or to quantitation of a known SERS signal, for example the signal obtained from known SERS nanotags. Portable readers have not previously been used to identify species such as melamine using SERS, in part because of concerns about the loss of spectral resolution with decreasing spectrometer size making it difficult to accurately assign bands within the Raman spectrum. In SERS-based assays for melamine, the predominance of a single band in the SERS spectrum, and its unique spectral position, mitigates the need for high spectral resolution.

Alternative reader embodiments include the inclusion of two sample holders on a single reader. In certain magnetic no-wash assay formats, a magnetic pre-concentration step is desired, to generate an initial "soft pellet". The pre-concentration step may consist of a simple magnetic tray for tubes, an typically has been implemented as a separate apparatus. Ideally, such an initial pre-concentration step (if required) could be carried out on the portable reader itself Thus, one sample holder on the reader could be used for magnetic pre-concentration, and the second could be used for laser interrogation and readout. The first holder could, in addition to magnetic pre-concentration, carry out any other steps required prior to sample analysis, including but not limited to mixing, agitation, heating, and cooling. Likewise, in a multiplexed assay described elsewhere herein, if two different excitation wavelengths are required, each can be coupled to a separate sample holder.

Software

In the case of a single-analyte assay, such as a melamine-only assay, it is not required to have a stored spectrum associated with the reader, since analyte identification may be made with reference to a single spectroscopic band. For multiplexed assays, it is typically necessary to have the spectral components of the individual analytes stored and available at the reader. A novel aspect of disclosed embodiments is the utilization of stored SERS spectra. When storing the Raman spectra of solids, as has been done previously for bulk chemical analysis using portable Raman instrumentation, there is only one spectrum to consider; the bulk Raman spectrum. However, in the case of SERS, numerous spectra are possible, since the SERS spectrum will depend upon multiple factors. For example, the SERS spectrum for an adsorbed species will change as function of coverage, since molecular orientation (which is reflected in the relative intensities of SERS-active vibrations) will vary with coverage. For example, a pancake-shaped molecule may lie flat at low coverage on the SERS surface, thus maximizing surface contact, or be bound edge-on at higher concentration. Likewise, relative SERS intensities will vary with the nature of the SERS substrate itself, since SERS intensities are dependent on the coupling of the excitation and scattered photon.

Other Related Fields

While the examples described herein relate to melamine, the compositions, methods, materials, reagents, assay formats, assay concepts, instruments, and software described herein are useful for detection, analysis and/or quantification measurements on a wide variety of analytes, including but not limited to chemical or pharmaceutical industry products such as adhesives, agricultural chemicals, antioxidants, biocides, catalysts, chelants, coal & fuel additives, construction chemicals, corrosion inhibitors, cosmetic additives, defoamers, drugs (and pro-drugs), dyes and organic pigments, elastomers, electronic chemicals, industrial enzymes, flame retardants, flavors, fragrances, food additives, foundry chemicals, gasoline additives, industrial & institutional cleaners, industrial coatings, ion exchange resins, laboratory chemicals, lubricant & functional fluid additives, synthetic lubricants & functional fluids, metal plating and finishing chemicals, mining chemicals, oil-field chemicals, paint additives, paper additives, pharmaceutical compositions, photographic chemicals, inorganic pigments, plastics additives, printing inks, refinery & pipeline chemicals, rubber processing chemicals, sealants, specialty polymers (engineering thermoplastics), specialty surfactants, textile specialties, thickeners, UV absorbers, and water management chemicals.

Likewise, disclosed embodiments also can be used for solid, liquid and gaseous pollutants, either as byproducts arising from the chemical or pharmaceutical industry processes, or more generally, environmental pollutants, whether naturally occurring or man-made.

Likewise, the concepts described herein can be used for detection, analysis, and/or quantification measurements related to or carried out on (i) seeds, (ii) whether alive or dead, organisms belonging to the kingdom Plantae, including but not limited to trees, herbs, bushes, grasses, vines, ferns, mosses, and algae, and (iii) non-animal products of agriculture, including but not limited to food, fibers, fuels, flowers, resins, and plastics.

In addition, the embodiments disclosed herein may be applicable to the field of molecular and cellular sensing (e.g., detecting and identifying) for public safety and homeland security, including but not limited to the detection, analysis, and/or quantification measurements related to or carried out on infectious biological agents (e.g. anthrax), highly toxic biomolecules (e.g. ricin), highly toxic molecules (e.g. sarin), or any other substances used to attack or intimidate individuals, groups of individuals, populations, societies or governments.

The disclosed methods can also be used for detection, analysis, and/or quantification measurements related to brand security, brand protection, trademark protection, product security, product identification, brand diversion, barcoding, grey market remediation, friend-or-foe analysis, product life cycle analysis, counterfeiting, anti-counterfeiting, forensic analysis of authenticity, authentication, biometrics, object tracking, chain-of-custody analysis, product tampering, anti-smuggling, smuggling detection, supply-chain tracking, product tracking, lost revenue recovery, product serialization, serialized authentication, freshness tracking, sell-by date tracking, and use-by date tracking.

Likewise, the disclosed embodiments have relevance to in vivo diagnostics, and in particular imaging, measurements, assays, and therapeutics-related tests that are carried out on intact live biological organisms, including but not limited to invertebrates, fish, amphibians, reptiles, birds, mammals, and plants.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the various embodiments have been particularly shown and described with reference to selected specific embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference for all matters disclosed therein.

EXAMPLES

The following examples are provided for illustrative purposes only and are not intended to limit the scope of the disclosed embodiments.

Example 1

Detection of Melamine in Water

Samples were prepared having 0.1 mM of each of the following: melamine, cyanuric acid, and cyanuric acid-melamine complex in water.

1 ml of 1×SERS-active Au colloid (60 nm) was placed in a screw top vial, and 2 μl, 5 μl, 8 μl, or 10 μl of each of the above listed solutions was added to the vial.

Figure 2:
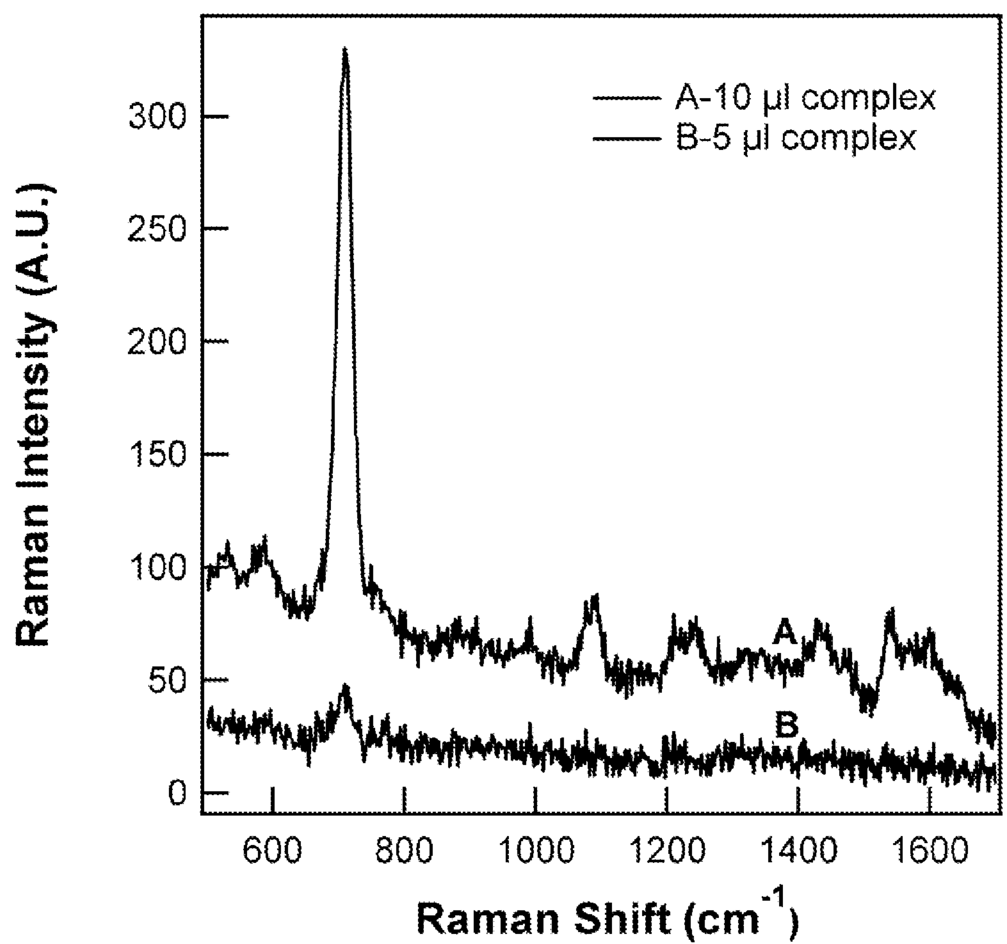
FIG. 2 is a graphic representation showing the detection of a SERS signal of a melamine/cyanuric acid complex in water.
Figure 3:
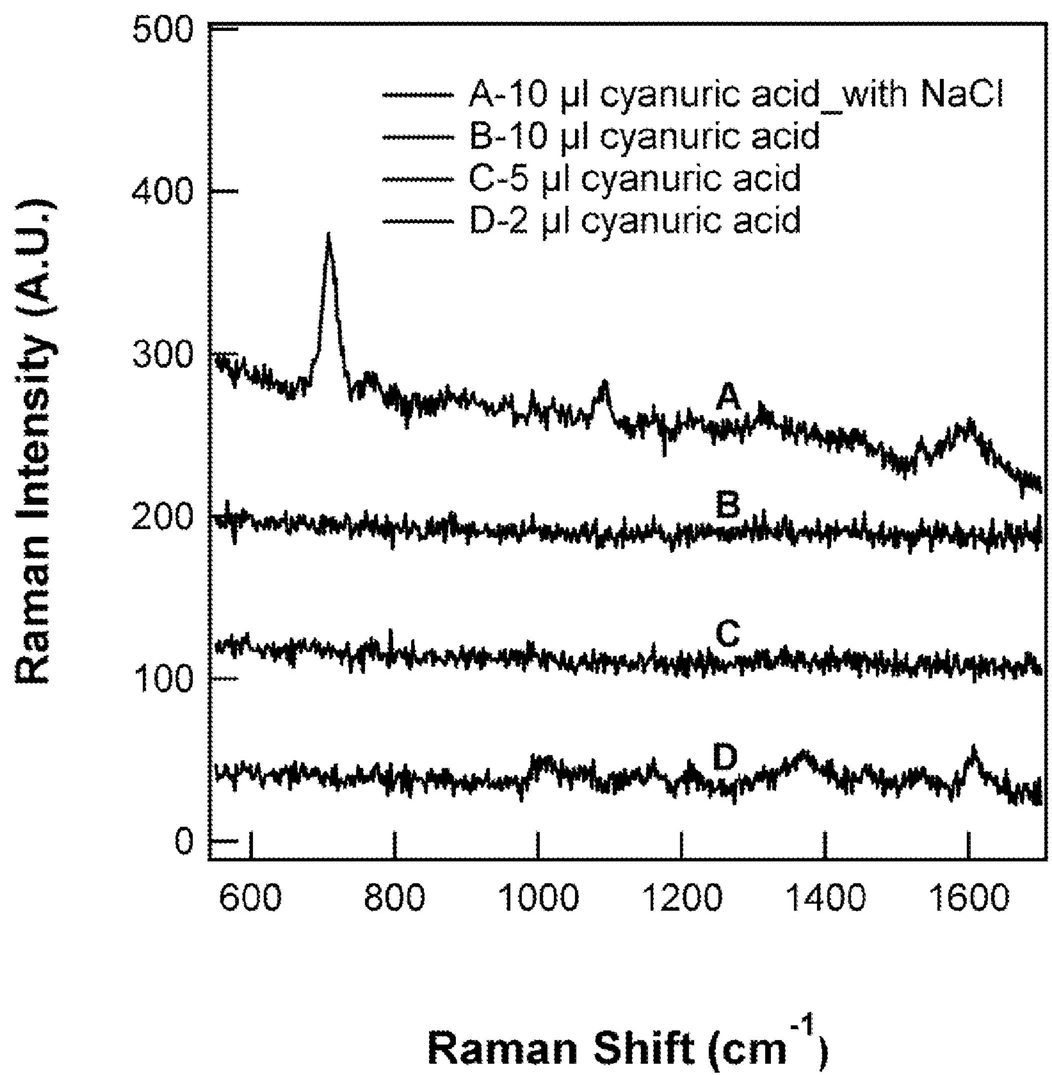
FIG. 3 is a graphic representation showing the detection of a SERS signal of cyanuric acid in water.

As shown in FIGS. 1-3 the addition of either melamine or melamine complex caused the colloid to aggregate and a SERS signal to be visible. Cyanuric acid showed no SERS signal until 20 μl of 1M NaCl was added to the sample. Adding more than 5 μl of melamine showed a decrease in signal, possibly due to a decrease in aggregation as the particle surfaces became independently coated with melamine inhibiting particle cross-linking.

Example 2

Detection of Melamine in Milk

Three different sized SERS colloids (40 nm, 67 nm, and 86 nm) were concentrated from 0.9 L to ~0.05 L.

Figure 4:
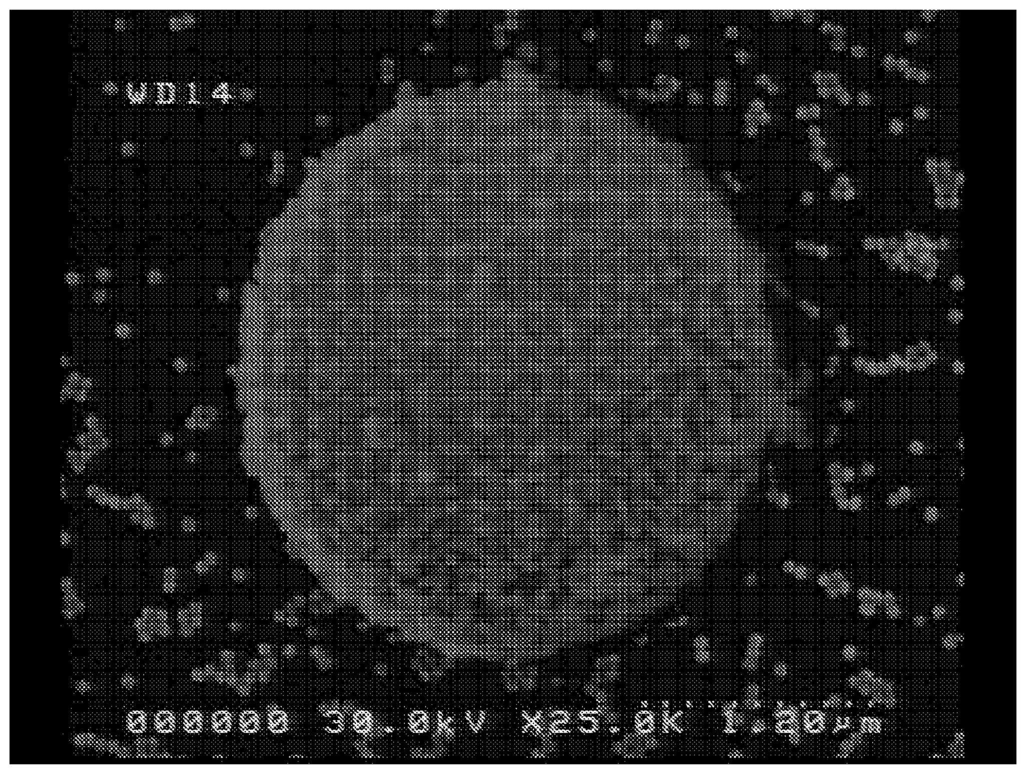
FIG. 4 is a scanning electron microscope image of a magnetic particle and associated Au nanoparticles.

100 μl Ademtech magnetic beads with amine coating were added to each batch of colloid and were mixed overnight. The particles changed from red to purple in color suggesting that the particles aggregated around the magnetic beads. As shown in FIG. 4, a scanning electron microscope image of a magnetic bead shows substantial coverage with Au particles.

The magnetic bead-Au colloid complexes were allowed to settle overnight and the supernatant was removed.

Figure 5:
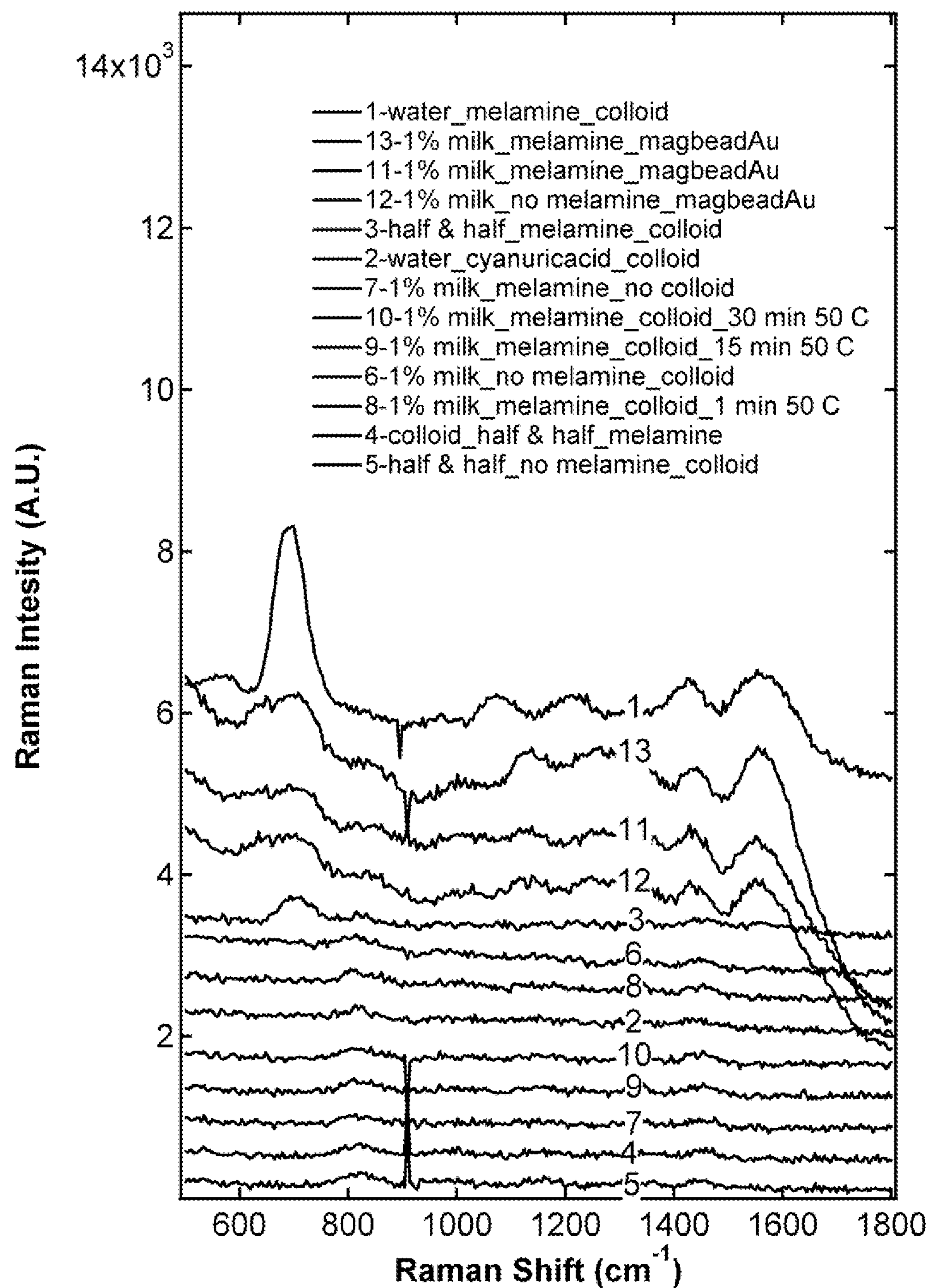
FIG. 5 is a graphic representation showing the detection of a SERS signal of melamine in dairy products.
Figure 6:
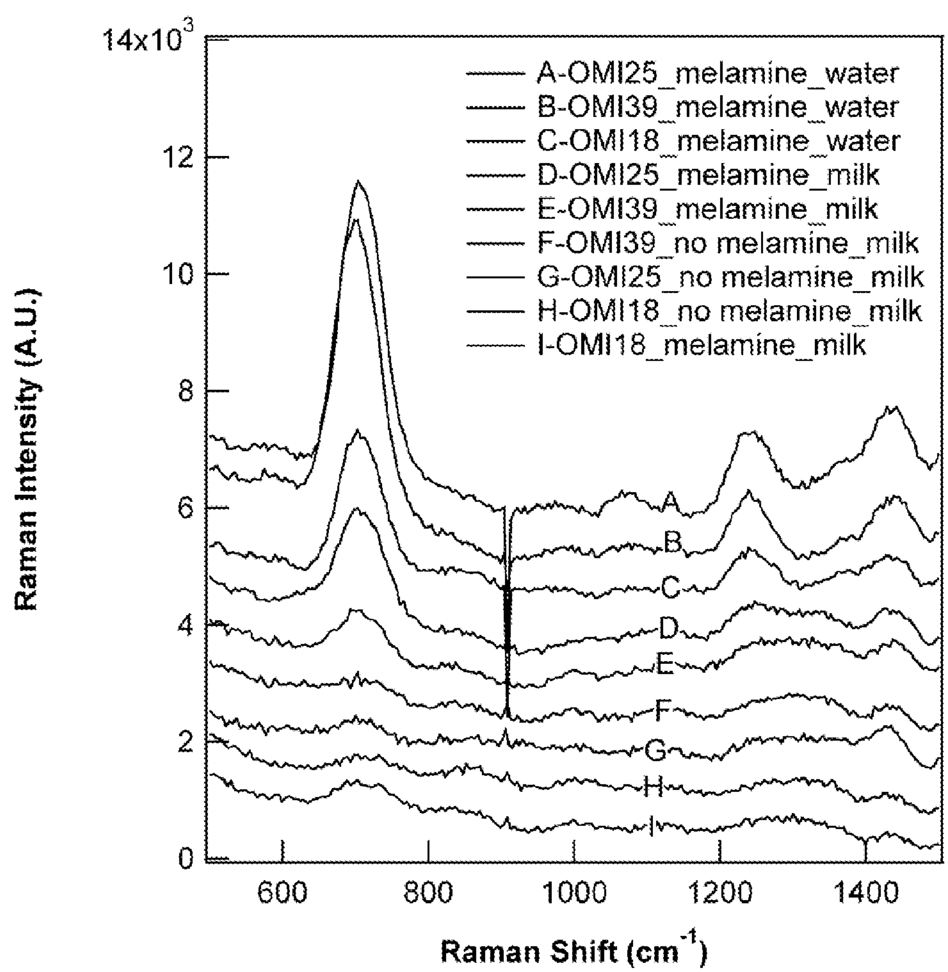
FIG. 6 is a graphic representation showing the detection of a SERS signal of melamine in powdered milk products.
Figure 7:
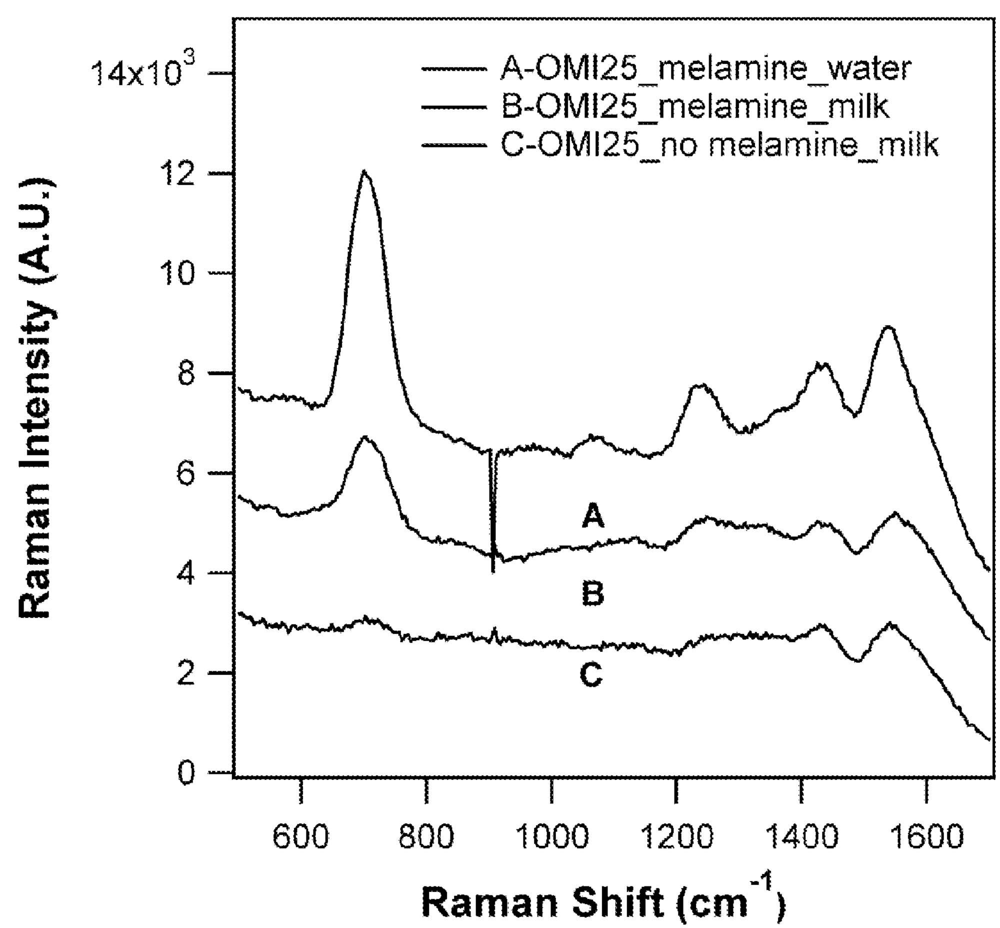
FIG. 7 is a graphic representation showing the detection of a SERS signal of melamine in powdered milk products.
Figure 8:
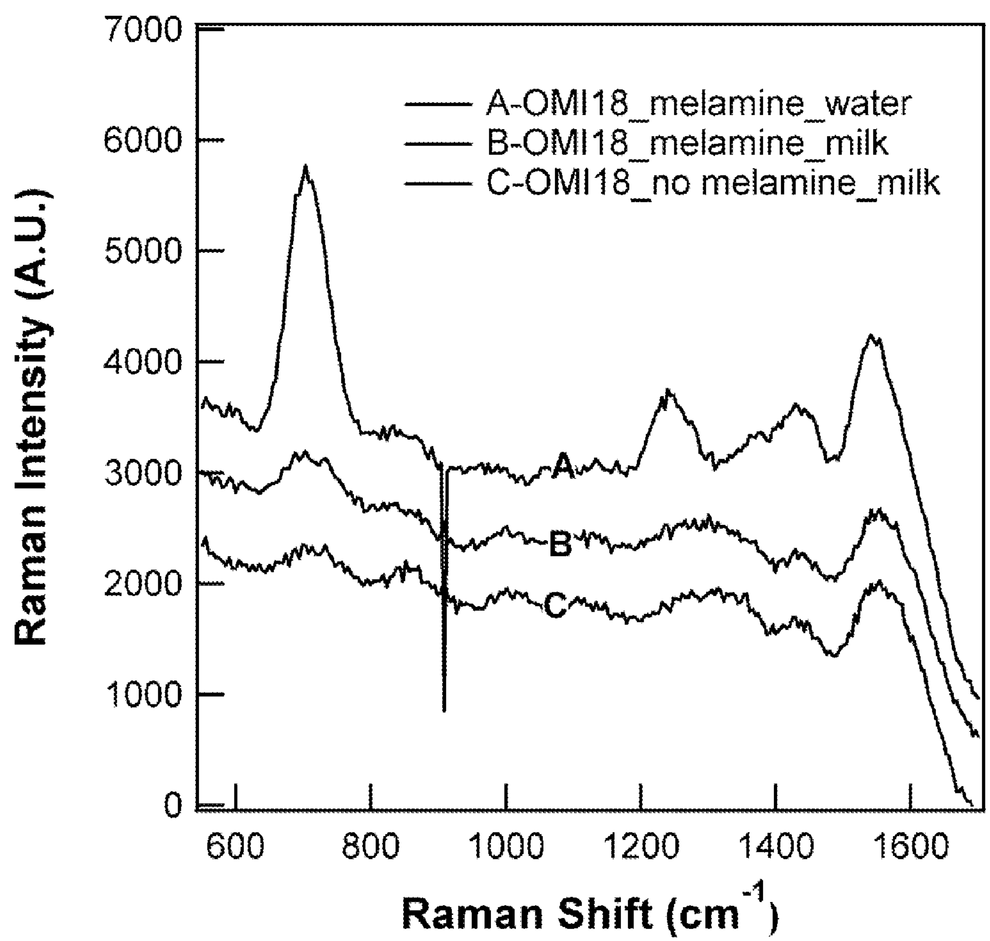
FIG. 8 is a graphic representation showing the detection of a SERS signal of melamine in powdered milk products.
Figure 9:
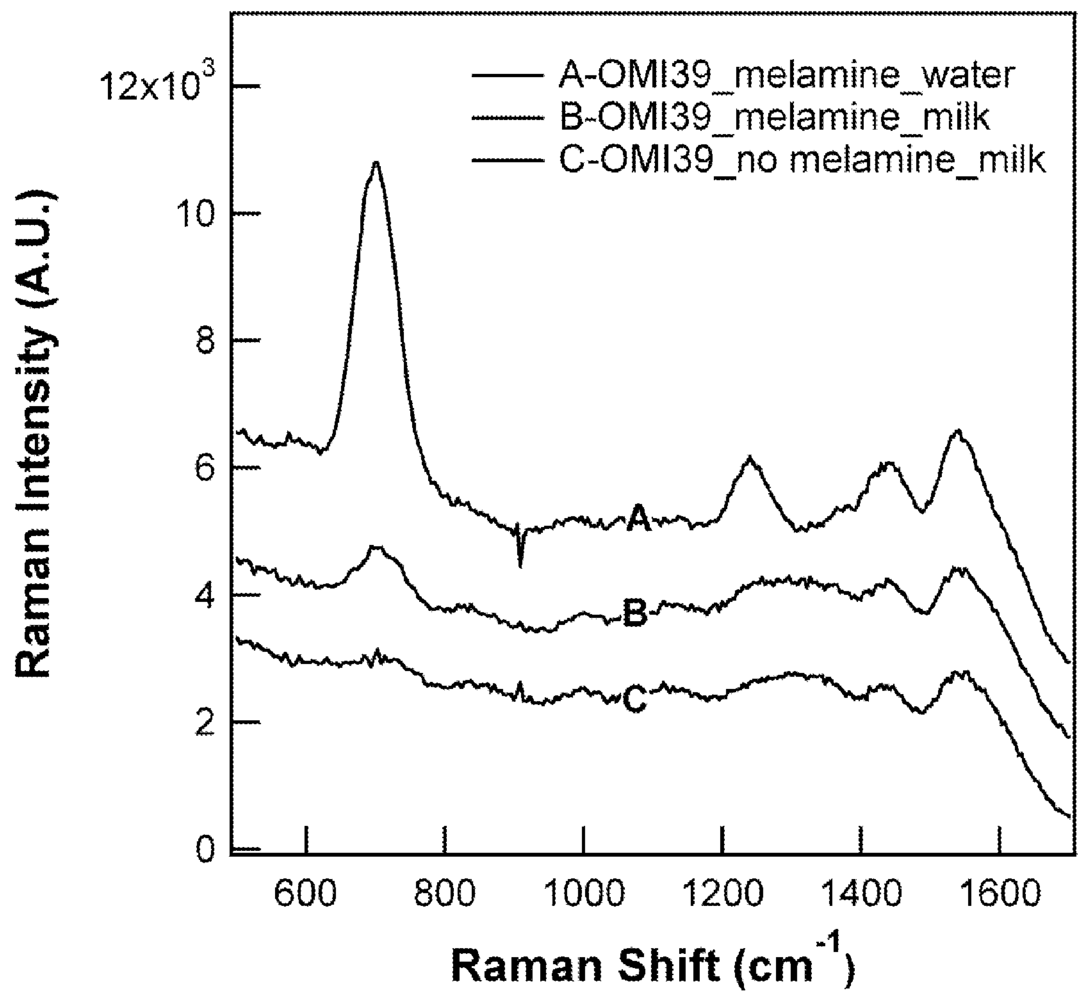
FIG. 9 is a graphic representation showing the detection of a SERS signal of melamine in powdered milk products.

The sample numbers listed below match the sample numbers in FIG. 5. The described experiments were performed in 0.2 ml Axygen tubes and were read in a 785 nm Raman instrument magnetic pull reader.

Sample 1—100 μl 67 nm colloid+10 μl 0.1 mM melamine

Sample 2—100 μl 67 nm colloid+10 μl 0.1 mM melamine

Sample 3—100 μl 67 nm colloid+10 μl 0.1 mM melamine+100 μl half and half (half and half added after melamine bound to colloid)

Sample 4—Premixed 100 μl half & half w/10 μl 0.1 mM melamine+100 μl 67 nm colloid (2×)

Sample 5—100 μl 67 nm colloid+100 μl half & half (no melamine)

Sample 6—100 μl 1% milk+50 μl 67 nm colloid (no melamine)

Sample 7—100 μl 1% milk premixed w/10 μl 0.1 mM melamine (no colloid)

Sample 8—100 μl 1% milk premixed w/10 μl 0.1 mM melamine+50 μl 67 nm colloid (2×)

Sample 9—Sample #8 on heatblock @ 50 C for 15 min

Sample 10—Sample #8 on heatblock @ 50 C for 30 min

Sample 11—100 μl 1% milk premixed w/10 μl 0.1 mM melamine+40 μl magnetic bead-Au complexes (used 67 nm colloid bead complexes)

Sample 12—100 μl 1% milk+40 μl magnetic bead-Au complexes (used 67 nm colloid bead complexes) (no melamine)

Sample 13—Sample #12; sonicated and added 100 μl 0.1 mM melamine

A peak is observed at 717 $cm^{-1}$ for melamine (sample #1), but in the presence of milk, there is not a great peak at 717 $cm^{-1}$. Milk is inhibiting the detection of melamine.

Example 3

Detection of Melamine in Powdered Milk

The experiment of Example 3 was performed with powdered milk. As shown in FIGS. 6-9 better detection of melamine was observed in powdered milk than in 1% milk or half & half.

Separate tubes were prepared to compare the different sizes of SERS-active Au colloid prepared as magnetic bead-Au colloid complexes. The colloid sizes used include 40 nm, 67 nm and 86 nm. Tubes were prepared with and without melamine, and with and without milk.

The particle sizes are labeled in the graph by manufacturing lot numbers and correlate to size as follows:

OMI 18: 40 nm
OMI 25: 67 nm
OMI 39: 86 nm

| Sample | Mag Bead Complex | Melamine | Milk/Water |
|---|---|---|---|
| 1 | OMI 25 | No | Milk |
| 2 | OMI 25 | Yes | Milk |
| 3 | OMI 25 | Yes | Water |
| 4 | OMI 18 | No | Milk |
| 5 | OMI 18 | Yes | Milk |
| 6 | OMI 18 | Yes | Water |
| 7 | OMI 39 | No | Milk |
| 8 | OMI 39 | Yes | Milk |
| 9 | OMI 39 | Yes | Water |

The reagents were added in the following order: melamine (50 ul 300 ppm) (in the "no melamine" sample 50 ul water was added), 80 ul milk or water, and 20 ul of the magnetic bead complexes.

OMI 18 tags (40 nm Au) were observed to give lower Raman signal in both water and milk than the larger colloid samples. OMI 25 (67 nm) particles appear to have superior performance characteristics.

Example 4

Detection of Melamine in Precipitated Powdered Milk

All sample tubes were prepared to contain 50 μl 300 ppm melamine, 75 μl milk, 5 μl HCl (if present and 5 additional μl milk if no HCl present) and 20 μl magnetic bead-Au particle complexes with all of the above 3 sizes; 40 nm, 67 nm, or 86 nm being tested.

Figure 10:
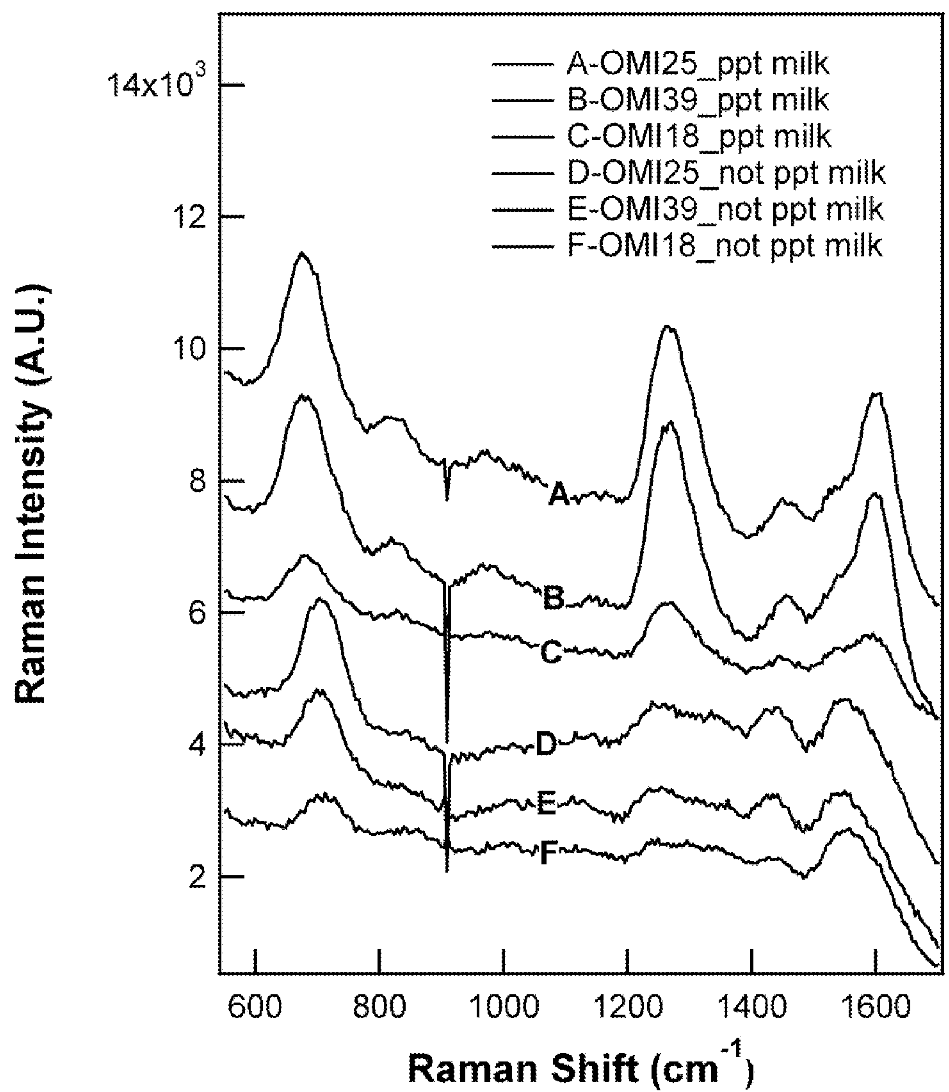
FIG. 10 is a graphic representation showing the detection of a SERS signal of melamine in powdered milk products with a precipitation step.

Melamine, milk, and HCl (if present) were added to a tube. If HCl added, then immediately a white precipitate would form. These precipitated samples were quickly spun down in a centrifuge for 10 sec, the pellet was left in the bottom of the tube and magnetic bead-Au complexes were added by pipette, but not mixed. The tubes were put in a magnetic tray after 1 min, and then read using a 785 nm Raman instrument. The resulting data is graphically displayed in FIG. 10.

Higher detected peaks were observed for the precipitated milk samples (labeled as ppt milk) than for the not precipitated milk samples (labeled as not ppt milk). Melamine peaks may be detected further out in spectrum (@~1300 cm-1) in the ppt milk samples, whereas these peaks are not observed in the non precipitated sample. Also, the 717 $cm^{-1}$ peak is shifted slightly left when the milk is precipitated with HCl acid.

Example 5

Detection of Melamine with Reference to an Internal Standard

An internal standard can be used to improve assay precision for direct SERS detection of melamine using colloidal gold particles. Assay precision is improved because the intensity of the SERS response is dependent upon the extent of colloid aggregation, yet colloid aggregation is a dynamic process that is difficult to control. Additionally, aggregation is impacted by multiple factors, including the amount of analyte molecule present, the amount of time the assay is allowed to react, and the ionic strength of the medium. By adding an internal SERS-active standard of known quantity and measuring SERS spectra from both of the standard and melamine, a simple ratiometric method may minimize the impact of inconsistent or unknown levels of colloid aggregation. As aggregation proceeds, the SERS intensity of each molecule is impacted in a similar manner.

In Example 5, melamine was detected by adding 5 μl 6.3 ppm melamine in water to 1 mL of 90 nm Au colloid, and acquiring a SERS measurement. Measurements of five separate samples were recorded and analyzed using a spectral fitting program. The relative signal intensities of melamine, the average signal for the five samples, and the standard deviation and coefficient of variation (CV) of the measurements are reported in Table 1. Table 2 shows the data for the same experiment, except 2 μl of a SERS-active standard, 10 ppm DPY (4,4'-dipyridyl) was added to each sample to serve as an internal standard. The spectral fitting software was used to distinguish the relative signals of melamine and DPY in each spectrum. The average melamine/DPY ratio is reported in Table 2 for five independent samples, as well as the corresponding standard deviation and CV. A significant improvement in CV is observed when the internal standard is used, from approximately 17% down to 5%.

TABLE 1

Melamine detected using 90 nm colloidal gold

| Melamine | Average | Standard Deviation | CV |
|---|---|---|---|
| 0.9909 | 0.9067 | 0.1538 | 17.0% |
| 0.7422 | | | |
| 0.9809 | | | |
| 0.7441 | | | |
| 1.0755 | | | |

TABLE 2

Melamine detected using 90 nm colloidal gold and DPY internal standard

| Melamine | DPY | Melamine/DPY | Average Melamine/DPY | Standard Deviation | CV |
|---|---|---|---|---|---|
| 1.3356 | 0.7030 | 1.9000 | 2.0188 | 0.1096 | 5.4% |
| 1.5423 | 0.7781 | 1.9821 | | | |
| 1.6568 | 0.8052 | 2.0576 | | | |
| 1.5112 | 0.7682 | 1.9672 | | | |
| 1.9276 | 0.8813 | 2.1873 | | | |

Figure 11:
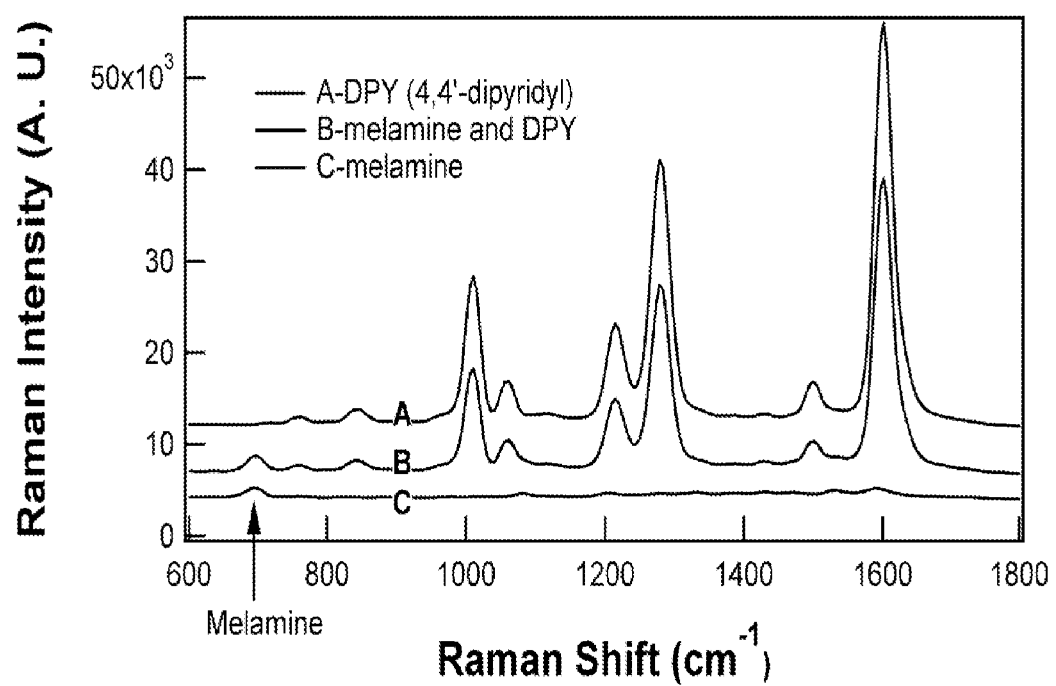
FIG. 11 is a graphic representation showing the detection of a SERS signal of melamine with a standard.

FIG. 11 graphically presents representative spectra from the internal standard (DPY), the melamine sample, and the sample containing both melamine and DPY.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method of detecting melamine comprising:
providing a quantity of SERS-active particles;
mixing a solution containing melamine with the SERS-active particles; and
detecting a surface enhanced Raman spectrum of the melamine.

2. The method of detecting melamine of claim 1 further comprising aggregating the SERS-active particles.

3. The method of claim 2 wherein the aggregation step comprises adding an aggregating agent to the mixture of melamine containing solution and SERS-active particles.

4. The method of claim 1 wherein the detecting step is performed without concentration of the SERS-active particles.

5. The method of claim 1 further comprising mixing a chaotropic agent having a higher affinity for a selected binding site than melamine into the solution containing melamine, wherein the chaotropic agent does not exhibit a SERS spectrum.

6. The method of claim 1 further comprising:
providing a quantity of a SERS-active standard having a known SERS spectrum;
mixing the solution containing melamine with the SERS-active particles and the SERS-active standard; and
detecting a surface enhanced Raman spectrum of the SERS-active standard.

7. The method of claim 6 wherein the SERS-active standard is deuterated melamine.

8. A method of detecting melamine comprising:
providing a quantity of SERS-active particles;
providing a quantity of magnetic particles;
associating one or more SERS-active particles with one or more magnetic particles;
mixing a solution containing melamine with the SERS-active particles and magnetic particles;
magnetically concentrating the magnetic particles; and
detecting a surface enhanced Raman spectrum of the melamine.

9. The method of detecting melamine of claim 8 wherein the SERS-active particles are associated with the magnetic particles through electrostatic attraction between the particles.

10. The method of detecting melamine of claim 8 wherein the SERS-active particles are associated with the magnetic particles before the SERS-active particles are associated with the magnetic particles.

11. The method of claim 8 further comprising mixing a chaotropic agent having a higher affinity for a selected binding site than melamine into the solution containing melamine, wherein the chaotropic agent does not exhibit a SERS spectrum.

12. The method of claim 8 further comprising:
providing a quantity of a SERS-active standard having a known SERS spectrum;

mixing the solution containing melamine with the SERS-active particles and the SERS-active standard; and detecting a surface enhanced Raman spectrum of the SERS-active standard.

13. A method of detecting a molecule of interest comprising:

providing a quantity of SERS-active particles;

providing a quantity of a SERS-active standard having a known SERS spectrum;

mixing a solution containing the molecule of interest with the SERS-active particles and the SERS-active standard;

detecting a surface enhanced Raman spectrum of the molecule of interest; and detecting a surface enhanced Raman spectrum of the SERS-active standard.

14. The method of claim 13 further comprising concentrating the SERS-active particles and the SERS-active standard.

15. The method of claim 14 further comprising:

providing a quantity of magnetic particles;

associating one or more of the SERS-active particles and a select quantity of the SERS-active standard with one or more magnetic particles; and magnetically concentrating the magnetic particles.

16. The method of claim 13 wherein the SERS-active standard is an analog of the molecule of interest.

17. The method of claim 16 wherein the SERS-active standard is deuterated melamine and the molecule of interest is melamine.

18. An assay system comprising:

a quantity of SERS-active particles;

a quantity of a SERS-active standard;

a container for mixing a solution of a molecule of interest with the SERS-active particles and the SERS-active standard; and a SERS reader configured to obtain a SERS spectrum of the molecule of interest and a SERS spectrum of the SERS-active standard.

19. The assay system of claim 18 further comprising: a quantity of magnetic particles; and a magnetic concentration apparatus.

20. The assay of system of claim 18 further comprising an aggregating agent.

21. The assay of system of claim 18 further comprising a chaotropic agent that does not exhibit a SERS spectrum.

22. The assay of system of claim 18 wherein the molecule of interest is melamine.

* * * * *